(12) United States Patent
Ko

(10) Patent No.: US 11,849,915 B2
(45) Date of Patent: Dec. 26, 2023

(54) SUCTION VALVE OF ENDOSCOPE

(71) Applicant: SML Med-Tech Solutions Limited, Hong Kong (CN)

(72) Inventor: Tsz Hang Ko, Hong Kong (CN)

(73) Assignee: SML Med-Tech Solutions Limited, Hong Kong (CN)

( * ) Notice: Subject to any disclaimer, the term of this patent is extended or adjusted under 35 U.S.C. 154(b) by 98 days.

(21) Appl. No.: 17/725,621

(22) Filed: Apr. 21, 2022

(65) Prior Publication Data

US 2022/0361734 A1 Nov. 17, 2022

(30) Foreign Application Priority Data

May 12, 2021 (HK) .......................... 32021030996.1

(51) Int. Cl.
*A61B 1/00* (2006.01)
*F16K 31/528* (2006.01)

(52) U.S. Cl.
CPC ...... *A61B 1/00068* (2013.01); *F16K 31/5284* (2013.01)

(58) Field of Classification Search
CPC .............. A61B 1/00068; A61B 1/015; A61M 2039/268; A61M 2039/2486; A61M 2039/0279; A61M 2039/2473; A61M 39/24; F16K 31/522; F16K 31/5284; F16K 5/0414; F16K 5/0407
See application file for complete search history.

(56) References Cited

U.S. PATENT DOCUMENTS

| | | | | |
|---|---|---|---|---|
| 4,293,117 A * | 10/1981 | Mueller | ............... | F16K 31/5284 74/57 |
| 4,666,124 A * | 5/1987 | Giacobbi | ................ | F16K 5/162 74/25 |
| 6,276,394 B1 * | 8/2001 | Smith | ................. | F16K 31/5284 251/56 |
| 2013/0043420 A1 * | 2/2013 | Case | ......................... | F16K 5/00 251/229 |
| 2018/0347709 A1 * | 12/2018 | Bowdery | ................ | B01L 3/567 |
| 2018/0361034 A1 * | 12/2018 | Tobien | ................ | F16K 31/5245 |
| 2020/0386330 A1 * | 12/2020 | Stanton | ................... | F16K 31/44 |
| 2021/0285604 A1 * | 9/2021 | Kim | ........................ | F17C 7/04 |

* cited by examiner

*Primary Examiner* — Kelsey E Cary

(74) *Attorney, Agent, or Firm* — George G. Wang; Bei & Ocean

(57) ABSTRACT

Disclosed is a suction valve for an endoscope, the endoscope including a first conduit and a second conduit, the suction valve including a shaft, a pressing unit, and a holding seat; wherein a first opening and a second opening are provided at a bottom and a sidewall of the shaft, respectively; the holding seat is sleeved in the shaft, and a middle portion of the shaft projects outward to form a ridge, the pressing unit including a bump, a first slot being provided at a sidewall of the holding seat, the bump being snap-fitted with the first slot.

10 Claims, 8 Drawing Sheets

SUCTION VALVE OF ENDOSCOPE

FIELD

The disclosure relates to medical instruments, and more particularly relates to a suction valve for an endoscope.

BACKGROUND

An endoscope is an inspection instrument commonly used in modern medical practices. The endoscope may access the stomach via the oral cavity, or access the inside of a human body via other tracts, or access the inside of a human body via a surgical incision, allowing for a medical practitioner to inspect and observe a lesion in the human body which cannot be detected by X-ray, thereby facilitating subsequent disease diagnosis. A gastrointestinal endoscope needs to be mated with a corresponding valve assembly in order for carrying out one or more endoscopy test procedures in a safe, effective, and rapid manner. A suction valve configured to facilitate suctioning of polyps and tissue fluid is one type of such valve assemblies.

In a conventional suction valve, a cap and a shaft are fixedly connected, wherein suction is realized by depressing the cap to actuate the shaft to move up and down. However, if improper direction or magnitude of force is applied when a practitioner depresses the cap, the shaft is prone to scrape or knock against an inner wall of the endoscope, causing damages to the endoscope and further reducing service life of the endoscope.

SUMMARY

The disclosure provides a suction valve for an endoscope, which overcomes the drawbacks in conventional suction valves caused by fixed connection between a cap and a shaft, i.e., if improper direction or magnitude of force is applied when a practitioner depresses the cap, the shaft is prone to scrape or knock against an inner wall of the endoscope, causing damages to the endoscope and further reducing the service life of the endoscope.

The disclosure provides a suction valve for an endoscope, wherein the endoscope comprises a first conduit and a second conduit, and the suction valve comprises a shaft, a pressing unit, and a holding seat; wherein a first opening and a second opening are provided at a bottom and a sidewall of the shaft, respectively, the first opening communicating with the first conduit; wherein the holding seat is sleeved in the shaft, and a middle portion of the shaft projects outward to form a ridge, the ridge being snap-fitted into the holding seat; wherein the pressing unit is connected to the shaft, the shaft being provided with a curved slide rail, the pressing unit being provided with a sliding ball at a position in contact with the curved slide rail, the pressing unit comprising a bump, a first slot being provided at a sidewall of the holding seat, the bump being snap-fitted with the first slot such that when the pressing unit is depressed, the bump moves in the first slot and the sliding ball slides along the curved slide rail to bring the shaft to rotate by a preset angle, such that the second opening communicates with the second conduit.

In the disclosure, the middle portion of the shaft projects outward to form a ridge. Since the ridge is snap-fitted into the holding seat, the shaft may be securely held by the holding seat to prevent up-and-down displacement and left-right skewing of the shaft, thereby preventing the shaft from scraping or knocking against an inner wall of the first conduit of the endoscope. When the pressing unit is depressed, the bump moves downward in the first slot. Since the shaft is locked by the holding seat, the downward movement of the bump brings the shaft to rotate, such that the sliding ball may slide downward along the curved slide rail; when the shaft is rotated by a preset angle, the second opening of the shaft commutates with the second conduit, thereby realizing suction. In the disclosure, since the shaft only performs a rotating motion and the gap between the shaft and the inner wall of the first conduit of the endoscope suffices for the shaft to rotate by any angle, even the practitioner depresses the pressing unit at an improper angle, the shaft does not squeeze towards the inner wall of the first conduit of the endoscope, thereby overcoming the drawbacks in conventional suction valves caused by fixed connection between the cap and the shaft, i.e., if improper direction or magnitude of force is applied when a practitioner depresses the cap, the shaft is prone to directly scrape or knock against an inner wall of the endoscope, causing damages to the endoscope and further reducing service life of the endoscope.

Optionally, the pressing unit comprises a cap and a spring; one end of the spring abuts against the holding seat, and the other end of the spring is connected to the cap; a second slot having a size adapted to the shaft is provided inside the cap, and the sliding ball is disposed at an inner sidewall of the second slot; the bump is disposed on an outer sidewall of the cap corresponding to the sliding ball. In this way, by virtue of the elasticity of the spring, the cap automatically resumes its original state, meanwhile bringing the shaft to rotate to its original position, thereby simplifying operation.

Optionally, the first slot has a length equal to a moving stroke of the second slot; when being depressed, the cap compresses the spring, and the bump moves in the first slot, bringing the second slot to move till covering the joint between the holding seat and the shaft. In this way, the suction valve achieves an improved sealing performance while realizing suction.

Optionally, an equal number of bumps, first slots, sliding balls, and curved slide rails are provided.

Optionally, two curved slide rails are provided, the two curved slide rails being arranged symmetrically about the center of the shaft.

Optionally, two third openings are provided in the sidewall of the cap, the two third openings being oppositely arranged. This arrangement increases the rate of air suction to maintain air pressure inside a patient's body.

Optionally, the suction valve comprises a sealing member, the sealing member being disposed between the spring and the holding seat and being tightly connected to the shaft. In this way, sealing performance during suction is enhanced, thereby achieving a good suction effect.

Optionally, a recessed groove having a size adapted to the bump is provided on an inner sidewall of the holding seat; the recessed groove is arranged diagonally above the first slot, and an indentation having a width identical to that of the bump is provided between the recessed groove and the first slot. In this way, assembly and disassembly of the cap is simplified, thereby facilitating operation.

Optionally, the preset angle refers to an angle formed by a connecting line between one endpoint of the curved slide rail and the center of the shaft and a connecting line between the other endpoint of the curved slide rail and the center of the shaft, the present angle being 90°.

Optionally, the suction valve further comprises a protective casing, the protective casing being sleeved with the holding seat. The protective casing may not only protect the holding seat, but also may cover the first slot to prevent foreign matters from entering the shaft from the first slot.

DETAILED DESCRIPTION

Figure 1:
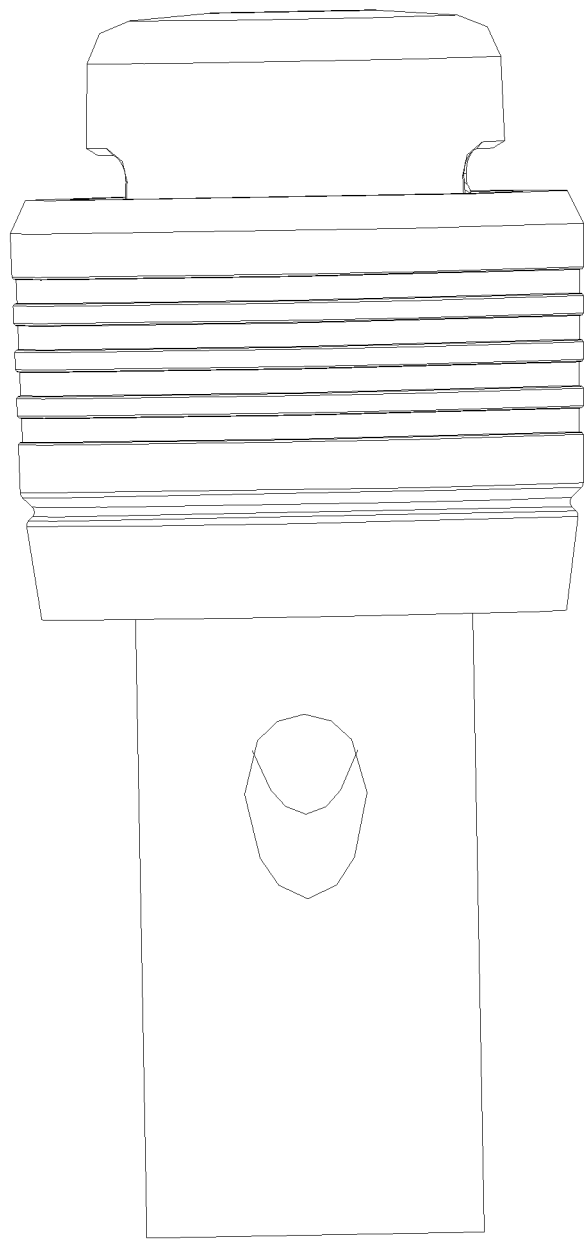
FIG. 1 is an overall structural schematic diagram of an endoscope according to the disclosure.
Figure 2:
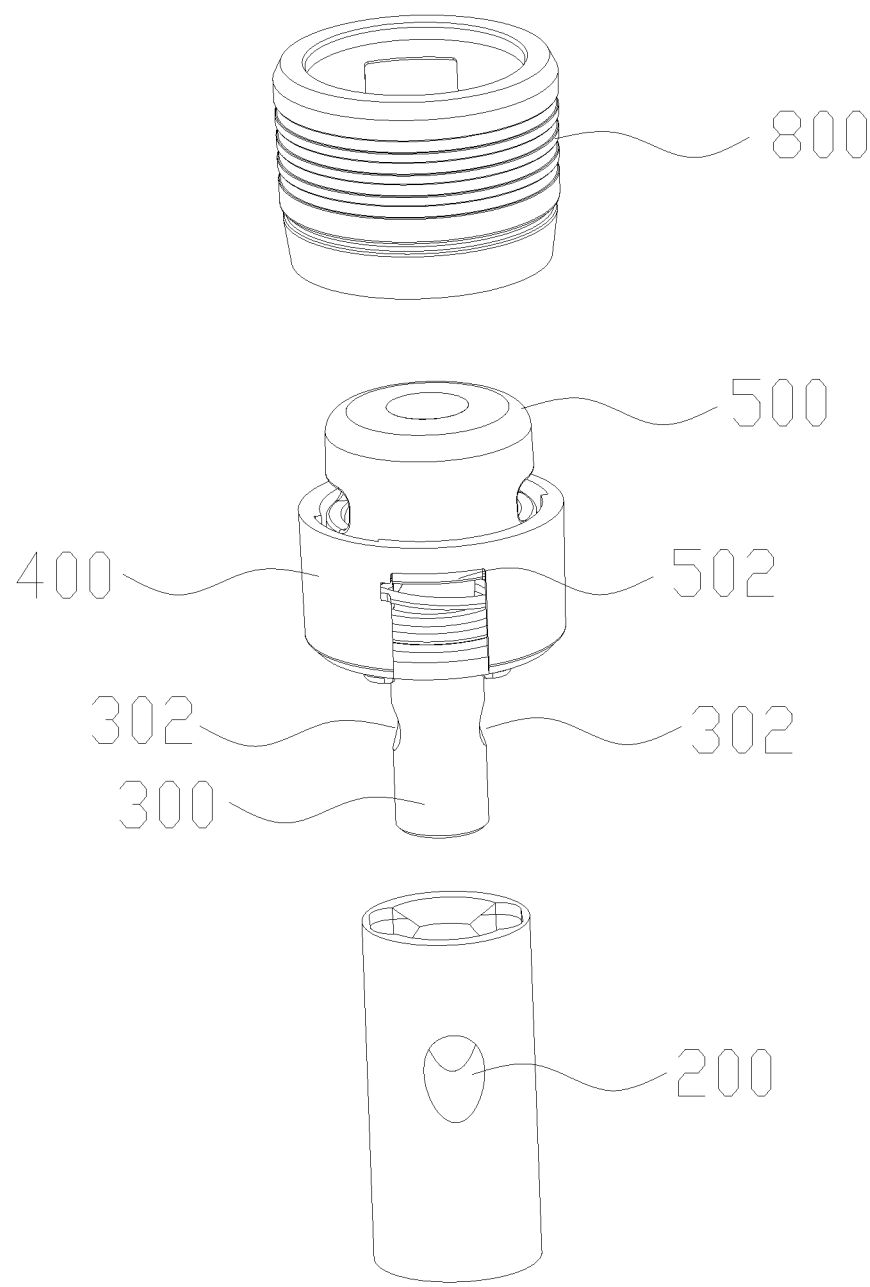
FIG. 2 is a structural schematic diagram of the endoscope before a suction valve is depressed according to the disclosure.
Figure 3:
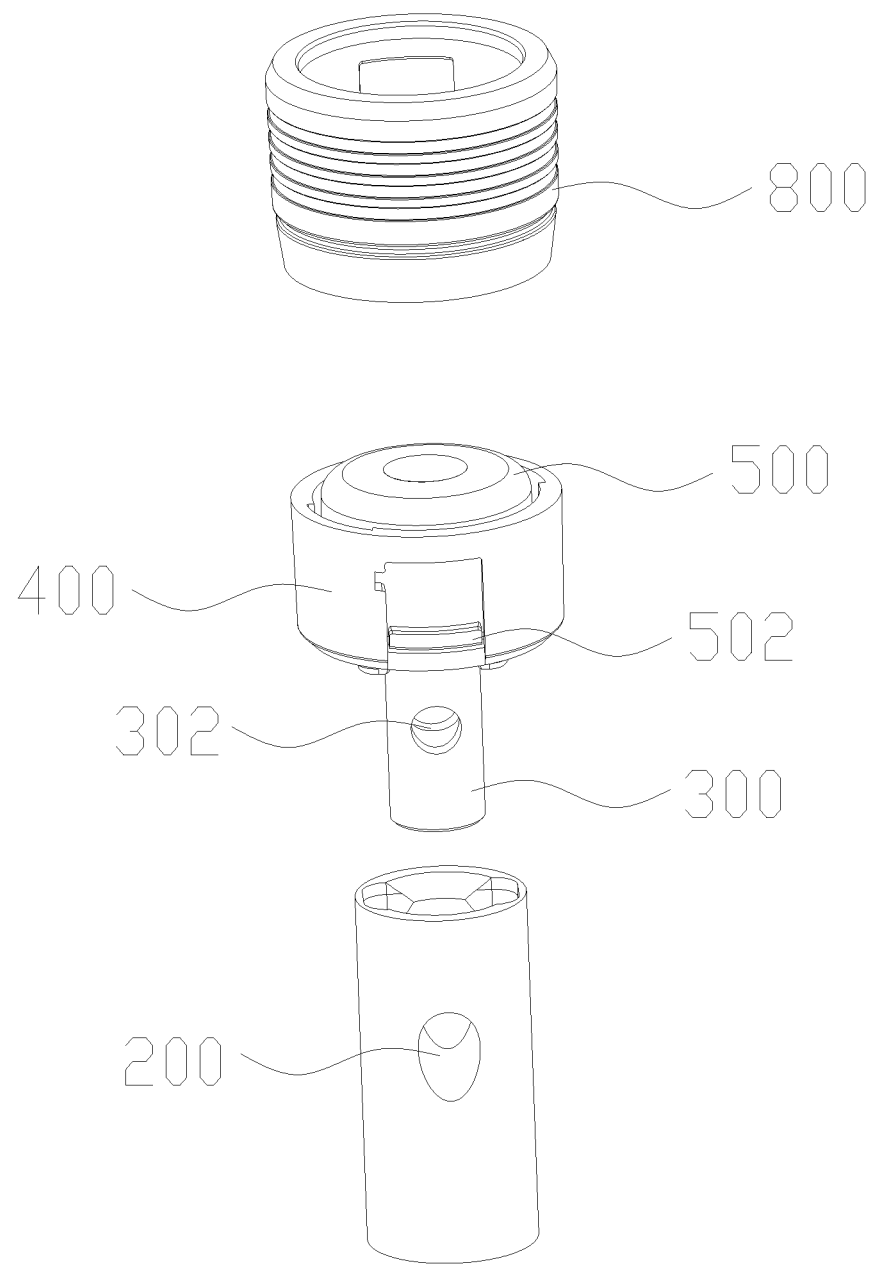
FIG. 3 is a structural schematic diagram of the endoscope after the suction valve is depressed according to the disclosure.
Figure 4:
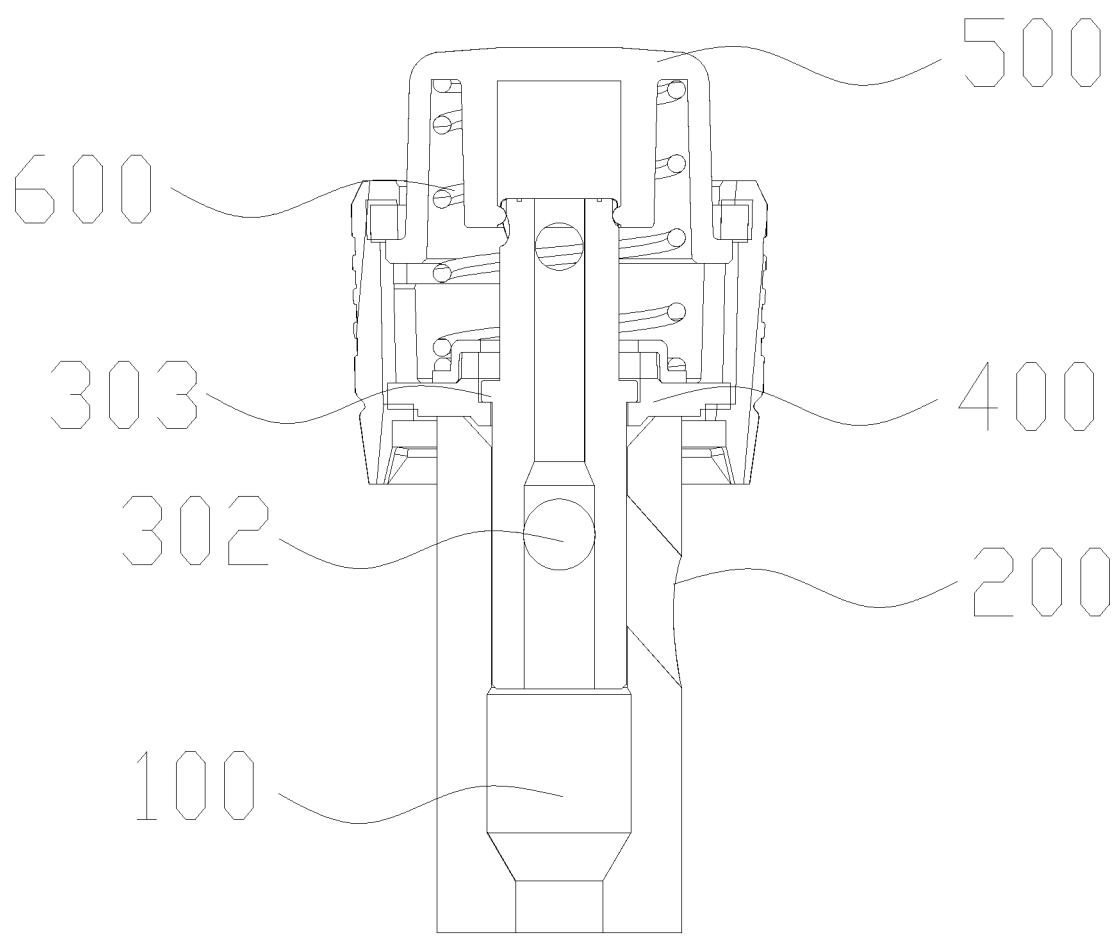
FIG. 4 is a sectional structural view of the endoscope before the suction valve is depressed according to the disclosure.
Figure 5:
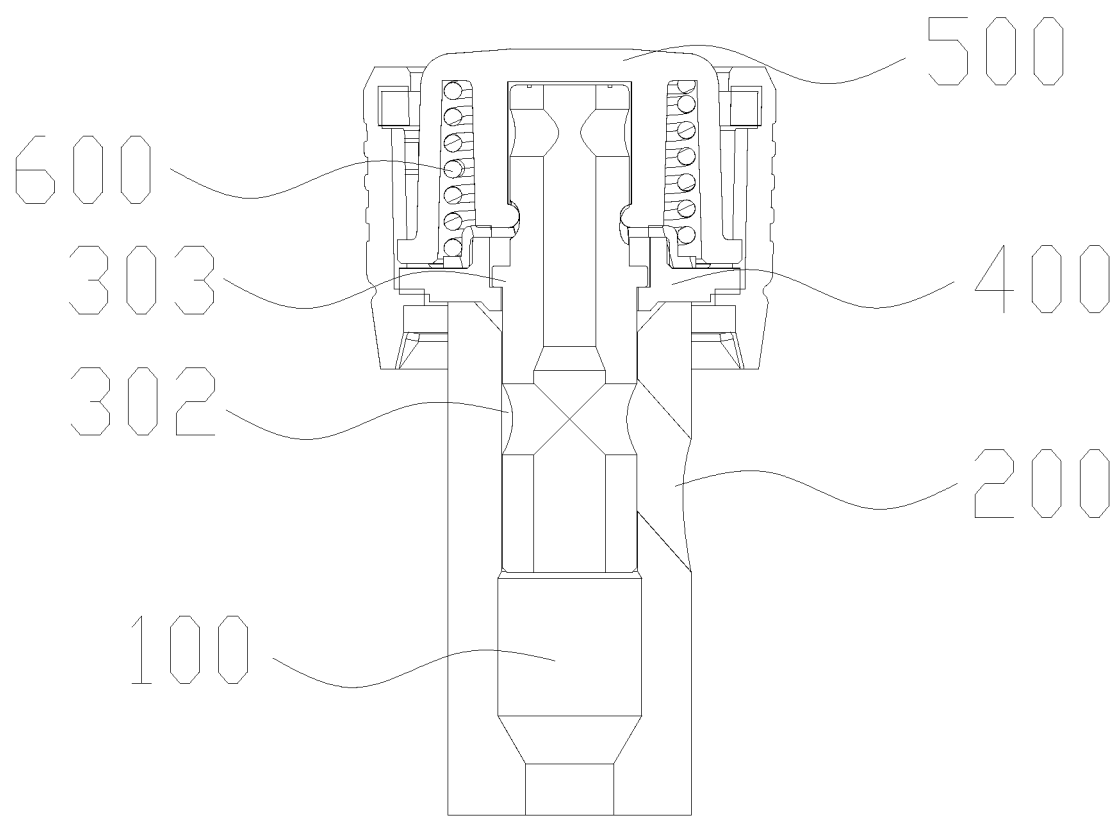
FIG. 5 is a sectional structural view of the endoscope after the suction valve is depressed according to the disclosure.
Figure 6:
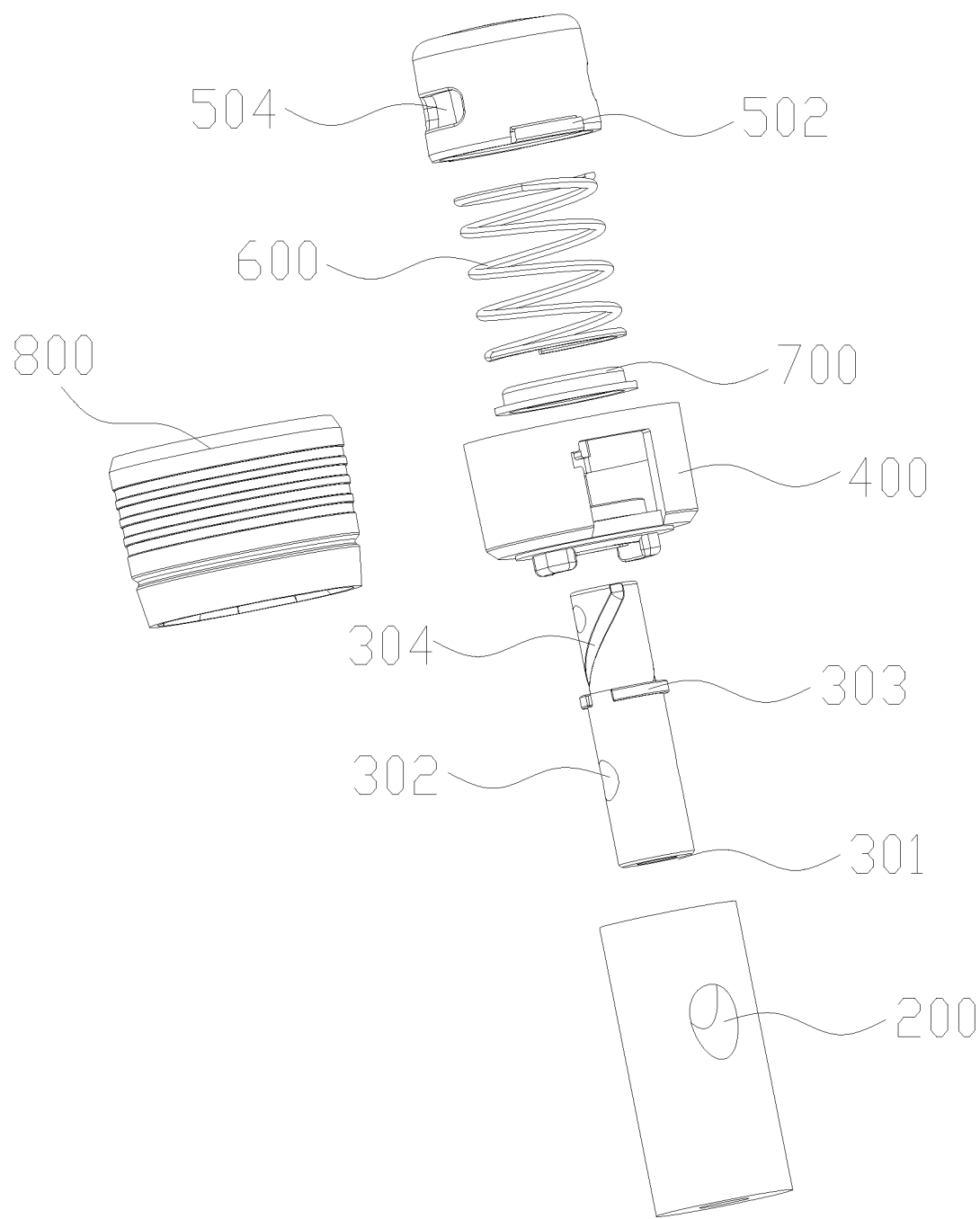
FIG. 6 is an exploded structural view of the suction valve for the endoscope according to the disclosure.
Figure 7:
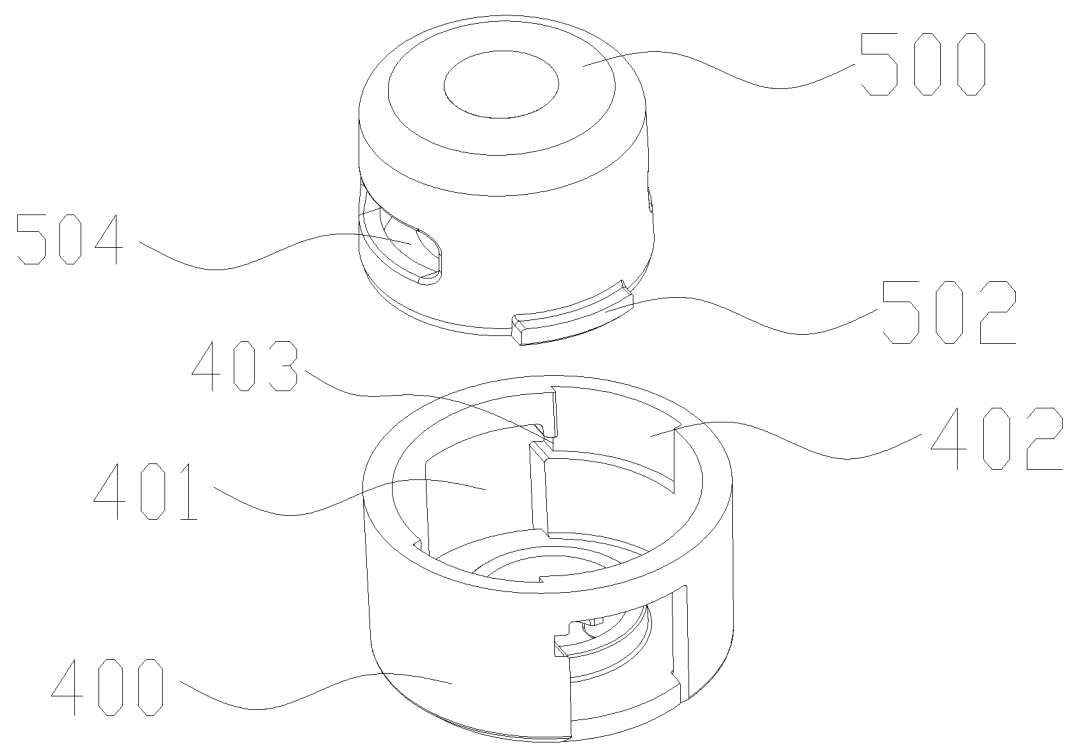
FIG. 7 is an assembled view of a holding seat and a cap according to the disclosure.
Figure 8:
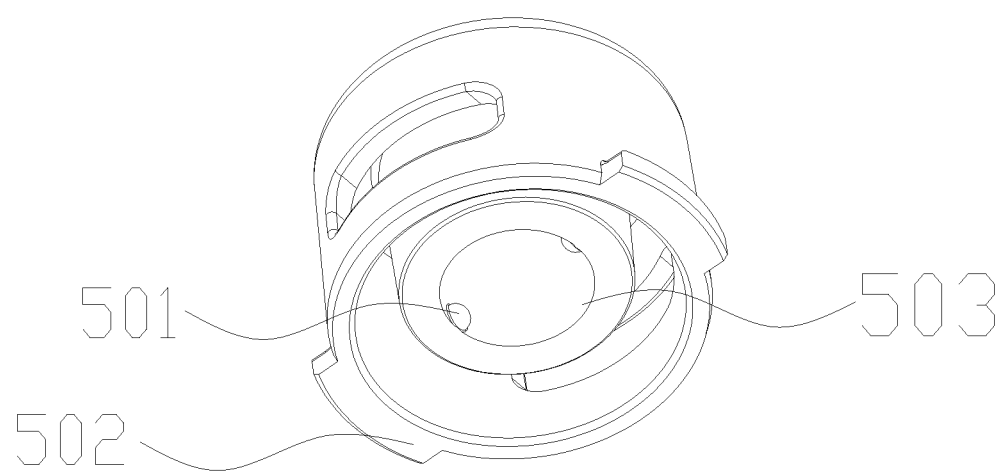
FIG. 8 is a structural schematic view of the cap according to the disclosure.

In a conventional suction valve, a cap and a shaft are fixedly connected, such that when a practitioner depresses the cap, an improper depressing angle easily occurs, a consequence of which is that the shaft would skew with respect to an inner wall of a conduit of the endoscope to directly scrape or knock against the inner wall of the conduit of the endoscope, thereby causing damages to the endoscope. Moreover, the endoscope might be operated by different practitioners, while different directions and magnitude of forces applied by the practitioners may act on different parts of the inner wall of the conduit of the endoscope via the shaft, which further aggravates wear of the endoscope and causes the shaft to be easily stuck. Furthermore, after long-term use of the endoscope, the scraping between the shaft and the inner wall of the endoscope likely produces chips, which, once being suctioned into the human body, will cause serious medical accidents.

In view of the above, an example of the disclosure provides a suction valve for an endoscope, which overcomes drawbacks of conventional suction valves caused by fixed connection between the cap and the shaft, i.e., if improper direction or magnitude of force is applied when a practitioner depresses the cap, the shaft is prone to directly scrape or knock against an inner wall of the endoscope, causing damages to the endoscope and further reducing the service life of the endoscope.

To make the objectives, features, and advantages of the disclosure more apparent and comprehensible, the technical solutions in the examples of the disclosure will be described clearly and sufficiently with reference to the drawings. It is apparent that the examples described below are only part of the embodiments of the disclosure, not all of them. All other embodiments derived by those skilled in the art based on the examples herein without exercise of inventive efforts fall within the scope of the disclosure.

Please refer to FIGS. 1 to 9. An example of the disclosure provides a suction valve for an endoscope, the endoscope comprising a first conduit 100 and a second conduit 200, the suction valve comprising a shaft 300, a pressing unit, and a holding seat 400; a first opening 301 and a second opening 302 are provided at a bottom and a sidewall of the shaft 300, respectively, the first opening 301 communicating with the first conduit 100; a holding seat 400 is sleeved in the shaft 300, and a middle portion of the shaft 300 projects outward to form a ridge 303, the ridge 303 being snap-fitted in the holding seat 400; the pressing unit is connected to the shaft 300, the shaft 300 being provided with a curved slide rail 304, the pressing unit being provided with a sliding ball 501 at a position in contact with the curved slide rail 304, the pressing unit comprising a bump 502, a first slot 401 being provided at a sidewall of the holding seat 400, the bump 502 being snap-fitted with the first slot 401 such that when the pressing unit is depressed, the bump 502 moves in the first slot 401 and the sliding ball 501 slides along the curved slide rail 304 to bring the shaft 300 to rotate by a preset angle, such that the second slot 302 communicates with the second conduit 200.

The suction valve is engaged with the endoscope. The first opening 301 communicates with the first conduit 100. In a practical application, the first conduit 100 is connected to a pneumatic pump of the endoscope. The second conduit 200 is inserted inside a human body to suction polyps and/or tissue liquids in the human body, wherein when the pressing assembly is not depressed, the second opening 302 and the second conduit 200 do not communicate. In this example, the ridge 303 of the shaft 300 is snap-fitted in the holding seat 400 to prevent up-and-down displacement and left-right skewing of the shaft 300; therefore, irrespective of whether the force or angle applied by the practitioner during operating is proper, scraping of the shaft 300 with respect to the inner wall of the conduit of the endoscope does not occur. Moreover, since the sliding ball 501 is provided for the pressing assembly at a position in contact with the shaft 300 and the bump 502 is snap-fitted with the first slot 401 in the holding seat 400, depressing of the pressing assembly brings the sliding ball 501 to slide along the curved slide rail 304. Since the pressing assembly can only move linearly up and down without rotation while the shaft 300 can only rotate without up-and-down movement, when the shaft 300 is rotated by a preset angle, the second opening 302 and the second conduit 200 communicate to realize suction. In addition, since the gap between the suction valve and an inner wall of the first conduit of the endoscope is set to 0.01 mm-0.03 mm in this example, which suffices to satisfy actual applications of the endoscope, even rotation of the shaft 300 in the inner wall of the conduits of the endoscope does not cause scraping with respect to the inner wall of the conduits.

In this example, the middle portion of the shaft 300 projects outward to form a ridge 303. The ridge 303 is snap-fitted in the holding seat 400 such that the shaft 300 may be securely held by the holding seat 400 to prevent up-and-down displacement or left-right skewing of the shaft 300, thereby preventing the shaft 300 from scraping and knocking against the inner wall of the first conduit of the endoscope. When the pressing assembly is depressed, the bump 502 moves downward in the first slot 401. Since the shaft 300 is locked by the holding seat 400, downward movement of the bump 502 brings the shaft 300 to rotate, such that the sliding ball 501 may slide downward along the curved slide rail 304; when the shaft 300 is rotated by a preset angle, the second opening 302 of the shaft 300 communicates with the second conduit 200 to realize suction. In the disclosure, since the shaft 300 can only perform a rotating motion and the gap between the shaft 300 and the inner wall of the first conduit of the endoscope suffices for the shaft 300 to rotate by any angle, even the practitioner depresses the pressing assembly at an improper angle, the shaft 300 does not squeeze the inner wall of the first conduit of the endoscope, thereby overcoming the drawbacks in conventional suction valves caused by fixed connection between the cap 500 and the shaft 300, i.e., if improper direction or magnitude of force is applied when the practitioner depresses the cap 500, the shaft 300 is prone to directly scrape or knock against an inner wall of the endoscope, causing damages to the endoscope and further reducing the service life of the endoscope.

What has been described above in detail is a first example of the suction valve for an endoscope according to the disclosure. Hereinafter, a second example of the suction valve for an endoscope will be described in detail.

Referring to FIGS. 1 to 9, an example of the disclosure provides a suction valve for an endoscope, the endoscope comprising a first conduit 100 and a second conduit 200; the suction valve comprises a shaft 300, a pressing assembly, and a holding seat 400; a first opening 301 and a second opening 302 are provided at a bottom and a sidewall of the shaft 300, respectively, the first opening 301 communicating with the first conduit 100; the holding seat 400 is sleeved in the shaft 300, wherein the middle portion of the shaft 300 projects outward to form a ridge 303, the ridge 303 being snap-fitted in the holding seat 400; the depressing unit is connected to the shaft 300, a curved slide rail 304 being provided for the shaft 300, a sliding ball 501 being provided for the pressing assembly at a position in contact with the curved slide rail 304, the pressing unit comprising a bump 502, a first slot 401 being provided in the sidewall of the holding seat 400, the bump 502 being snap-fitted with the first slot 401 such that when the pressing assembly is depressed, the bump 502 moves in the first slot 401, and the sliding ball 501 moves along the curved slide rail 304, bringing the shaft 300 to rotate by a preset angle, such that the second opening 302 communicates with the second conduit 200.

Furthermore, the pressing unit in this example comprises a cap 500 and a spring 600; one end of the spring 600 abuts against the holding seat 400, and the other end of the spring 600 is connected to the cap 500; a second slot 503 having a size adapted to the shaft 300 is provided inside the cap 500, the sliding ball 501 is provided at an inner sidewall of the second slot 503; the bump 502 is provided on an outer sidewall of the cap 500 corresponding to the sliding ball 501. By arranging the spring 600, the depressed cap 500 may automatically resume its original state by virtue of elasticity of the spring 600, which facilitates operation. It is noted that the first slot 401 has a length equal to a moving stroke of the second slot 503, such that when the cap 500 is depressed, the cap 500 compresses the spring 600, and the bump 502 moves in the first slot 401, bringing the second slot 503 to move till covering the joint between the holding seat 400 and the shaft 300; when the bump 502 moves from the utmost top end of the first slot 401 to the utmost bottom end of the first slot 401, the second slot 503 exactly covers the joint between the holding seat 400 and the shaft 300. In this way, sealing performance of the suction valve during suction is improved.

To further improve sealing performance of the section valve during suction, a sealing member 700 needs to be provided between the spring 600 and the holding seat 400, the sealing member 700 being tightly connected with the shaft 300. In this way, the sealing performance during suction is further improved to achieve a good suction effect.

It is noted that in this example, the preset angle refers to an angle formed by a connecting line between one endpoint of the curved slide rail 304 and the center of the shaft 300 and a connecting line between the other endpoint of the curved slide rail 304 and the center of the shaft 300. Of course, presetting of the angle needs to further consider the length of the curved slide rail 304 as well as the downward moving stroke of the cap 500. Given the angle formed by the connecting lines between the respective two end points of the curved slide rail 304 and the center of the shaft 300, the downward moving stroke of the cap 500 needs to be specified based on the angle; in this way, the suction valve achieves a good sealing performance while realizing suction. In this example, the value of the preset angle is set to 90°.

Figure 9:
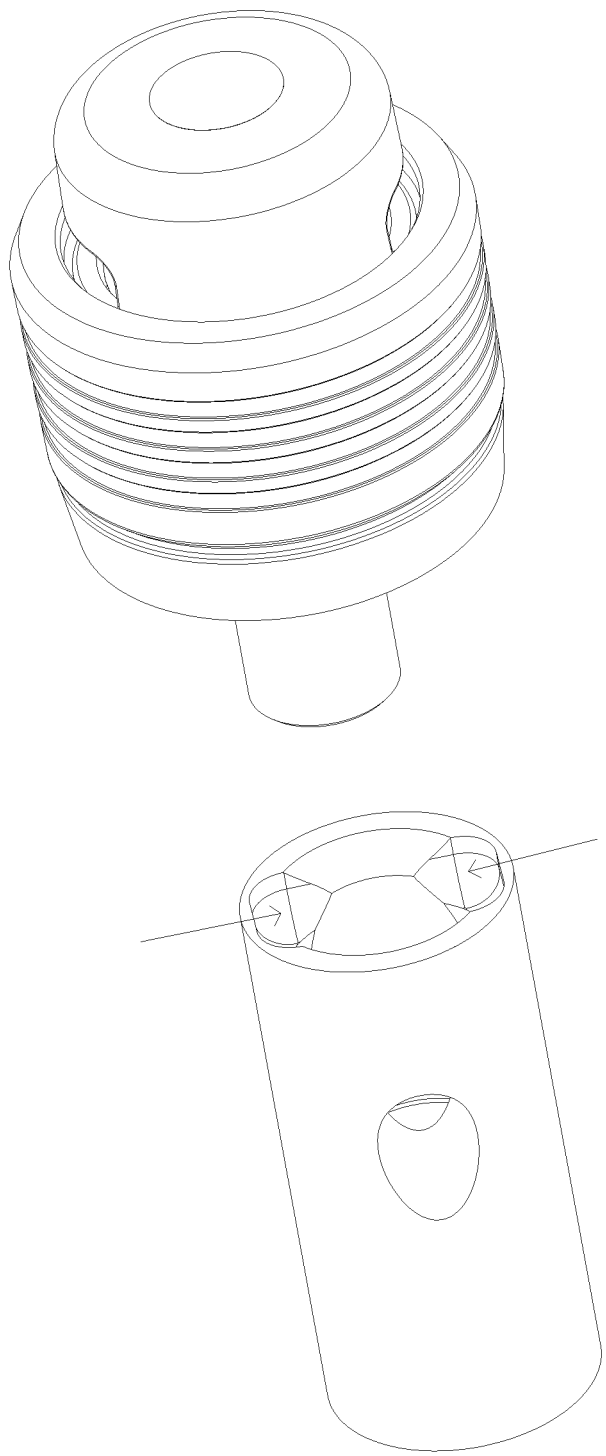
FIG. 9 is schematic diagram of an endoscope coupler according to the disclosure.

It is noted that in this example, two second openings 302 are provided due to the symmetrical profile of a conventional endoscope coupler. In FIG. 9, the endoscope coupler is indicated by the arrows. In this example, the preset angle is 90°, but the endoscope only has a single conduit, i.e., the second conduit 200. Therefore, providing of the two openings 302 facilitates the practitioner's assembly work, i.e., coupling match is not an issue to consider, thereby allowing for coupling in both forward and reverse directions.

Furthermore, an equal number of bumps 502, first slots 401, sliding balls 501, and curved slide rails 304 are provided. In this example, two bumps 502, two first slots 401, two sliding balls 501, and two curved slide rails 304 are provided, wherein the bumps 502 and the first slots 401 are in one-to-one correspondence, and the sliding balls 501 and the curved slide rails 304 are in one-to-one correspondence. The two curved slide rails 304 are arranged symmetrically about the center of the shaft 300 so as to cooperate with 90° rotation of the shaft 300, thereby facilitating the practitioner to operate.

Furthermore, a through hole (not shown) is disposed directly above the second opening 302 of the shaft 300. Two third openings 504 are oppositely arranged in the sidewall of the cap 500. When the suction valve is not depressed, a pneumatic pump in the endoscope may suction the ambient air via the third openings 504 and the through hole so as to prevent undesired suctioning of the air inside the patient body. Providing of the two third openings 504 and the through hole enables the pneumatic pump to suction the ambient air rapidly and meanwhile the increased rate of air suction facilitates maintaining of the air pressure inside the patient body.

Furthermore, to facilitate assembly and disassembly of the cap 500 into/from the holding seat 400, a recessed groove 402 having a size adapted to the bump 502 is provided at the inner sidewall of the holding seat 400; the recessed groove 402 is arranged diagonally above the first slot 401, and an indentation 40 having a width identical to that of the bump 502 is provided between the recessed groove 402 and the first slot 401. To assemble the cap, the two bumps 502 disposed at the outer sidewall of the cap 500 are respectively inserted into the recessed grooves 402; then, the cap 500 is twisted to enter the first slots 401 via corresponding indentations 403, realizing snap-fitting between the bumps 502 and the first slots 401. To disassemble the cap, the two bumps 502 are moved into corresponding indentations 403 and then the cap 500 is twisted to cause the bumps 502 to be inserted into corresponding recessed grooves 402 again; now, the cap 500 is disassembled just by pulling. In this way, assembly and disassembly of the cap 500 are simplified, which facilitates operation.

Furthermore, in this example, a protective casing 800 is further provided. The protective casing 800 is sleeved with the holding seat 400. The sleeving between the protective casing 800 and the holding seat 400 may not only protect the holding seat 400, but also may cover the first slots 401 to prevent foreign matters from entering the shaft 300 via the first slots 401.

In this example, the middle portion of the shaft 300 projects outward to form a ridge 303. The ridge 303 is snap-fitted in the holding seat 400, such that the shaft 300 may be securely held by the holding seat 400 to prevent the shaft 300 from up-and-down displacement or left-right skewing, thereby further preventing the shaft 300 from scraping and knocking against the inner wall of the conduit of the endoscope. When the pressing unit is depressed, the bump 502 moves downward in the first slot 401. Since the shaft 300 is locked by the holding seat 400, downward movement of the bump 502 brings the shaft 300 to rotate such that the sliding ball 501 may slide downward along the curved slide rail 304; when the shaft 300 is rotated by the preset angle, the second opening 302 of the shaft 300 communicates with the second conduit 200; in this way, suction is realized. In the disclosure, since the shaft 300 only performs a rotating motion and the gap between the shaft 300 and the inner wall of the conduit of the endoscope suffices for the shaft 300 to rotate by any angle, even the practitioner depresses the pressing unit at an improper angle, the shaft 300 does not squeeze towards the inner wall of the conduit of the endoscope, thereby overcoming the drawbacks in conventional suction valves caused by fixed connection between the cap 500 and the shaft 300, i.e., if improper direction and magnitude of force is applied when a practitioner depresses the cap 500, the shaft 300 is prone to directly scrape or knock against the endoscope inner wall, causing damages to the endoscope and further reducing service life of the endoscope.

In the description of the disclosure, it needs to be understood that the orientational or positional relationships indicated by the terms "center," "upper," "lower," "left," "right," "vertical," "horizontal," "inner," and "outer," etc. refer to the orientational and positional relationships illustrated in the drawings, which are intended only for facilitating or simplifying description of the disclosure, not for indicating or implying that the referred to devices or elements have to possess those specific orientations and have to be configured and operated with such specific orientations; therefore, they should not be understood as limitations to the disclosure. Besides, the terms "first," "second" and "third" are only used for description purposes, which should not be understood as indicating or implying an importance.

In the description of the examples of the disclosure, it is noted that unless otherwise explicitly provided and limited herein, the terms such as "mount," "attach," "connect" as well as their variations should be understood broadly, which, for example, may refer to a secured connection, a detachable connection, or an integral connection; which may be a mechanical connection or an electrical connection, which may be a direct connection or an indirect connection via an intermediate medium, and which may also be a communication between the insides of two elements. To a person of normal skill in the art, specific meanings of the above terms in the examples of the disclosure may be understood dependent on specific situations.

The examples described above are only embodiments of the disclosure, not intended for limiting. Although the disclosure has been described in detail with reference to the foregoing examples, a person of normal skill in the art would understand that any skilled person in the art may make modifications to the technical solutions described in the above examples, or make equivalent substitution to part of the technical features therein; however, such modifications or substitutions do not cause the essence of the corresponding technical solution to depart from the spirit and scope of the technical solutions in the examples of the disclosure.

I claim:

1. A suction valve for an endoscope, wherein the endoscope comprises a first conduit and a second conduit, and the suction valve comprises a shaft, a pressing unit, and a holding seat;
    wherein a first opening and a second opening are provided at a bottom and a sidewall of the shaft, respectively, the first opening communicating with the first conduit;
    wherein the holding seat is sleeved in the shaft, and a middle portion of the shaft projects outward to form a ridge, the ridge being snap-fitted into the holding seat;
    and wherein the pressing unit is connected to the shaft, the shaft being provided with a curved slide rail, the pressing unit being provided with a sliding ball at a position in contact with the curved slide rail, the pressing unit comprising a bump, a first slot being provided at a sidewall of the holding seat, the bump being snap-fitted with the first slot such that when the pressing unit is depressed, the bump moves in the first slot and the sliding ball slides along the curved slide rail to bring the shaft to rotate by a preset angle, such that the second opening communicates with the second conduit.

2. The suction valve for an endoscope according to claim 1, wherein the pressing unit comprises a cap and a spring;
    wherein one end of the spring abuts against the holding seat, and the other end of the spring is connected to the cap;
    wherein a second slot having a size adapted to the shaft is provided inside the cap, and the sliding ball is disposed at an inner sidewall of the second slot;
    and wherein the bump is disposed on an outer sidewall of the cap corresponding to the sliding ball.

3. The suction valve for an endoscope according to claim 2, wherein the first slot has a length equal to a moving stroke of the second slot;
    and wherein when being depressed, the cap compresses the spring, and the bump moves in the first slot, bringing the second slot to move till covering a connection between the holding seat and the shaft.

4. The suction valve for an endoscope according to claim 2, wherein an equal number of bumps, first slots, sliding balls, and curved slide rails are provided.

5. The suction valve for an endoscope according to claim 4, wherein two curved slide rails are provided, the two curved slide rails being arranged symmetrically about the center of the shaft.

6. The suction valve for an endoscope according to claim 2, wherein two third openings are provided in the sidewall of the cap, the two third openings being oppositely arranged.

7. The suction valve for an endoscope according to claim 2, wherein the suction valve comprises a sealing member, the sealing member being disposed between the spring and the holding seat and being tightly connected to the shaft.

8. The suction valve for an endoscope according to claim 1, wherein a recessed groove having a size adapted to the bump is provided on an inner sidewall of the holding seat;
    and wherein the recessed groove is arranged diagonally above the first slot, and an indentation having a width identical to that of the bump is provided between the recessed groove and the first slot.

9. The suction valve for an endoscope according to claim 1, wherein the preset angle refers to an angle formed by a connecting line between one endpoint of the curved slide rail and the center of the shaft and a connecting line between the other endpoint of the curved slide rail and the center of the shaft, the present angle being 90°.

10. The suction valve for an endoscope according to claim 1, further comprising a protective casing, the protective casing being sleeved with the holding seat.

\* \* \* \* \*